(12) United States Patent
Seiler et al.

(10) Patent No.: US 8,784,537 B2
(45) Date of Patent: Jul. 22, 2014

(54) AMINE-CONTAINING ABSORPTION MEDIUM, PROCESS AND APPARATUS FOR ABSORPTION OF ACIDIC GASES FROM GAS MIXTURES

(75) Inventors: Matthias Seiler, Griesheim (DE); Rolf Schneider, Gründau-Rothenbergen (DE); Jörn Rolker, Alzenau (DE); Daniel Dembkowski, Essen (DE); Manfred Neumann, Marl (DE); Daniel Witthaut, Wehrheim (DE); Michael Keup, Marl (DE); Volker Brehme, Nottuln (DE); Muhammad Irfan, Erlensee (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/884,840

(22) PCT Filed: Nov. 10, 2011

(86) PCT No.: PCT/EP2011/069787
§ 371 (c)(1),
(2), (4) Date: May 31, 2013

(87) PCT Pub. No.: WO2012/062830
PCT Pub. Date: May 18, 2012

(65) Prior Publication Data
US 2013/0247758 A1   Sep. 26, 2013

(30) Foreign Application Priority Data

Nov. 12, 2010 (DE) .......................... 10 2010 043 838
Jun. 10, 2011 (DE) .......................... 10 2011 077 377

(51) Int. Cl.
*B01D 53/14* (2006.01)
(52) U.S. Cl.
USPC ................. 95/183; 95/236; 96/234; 252/60; 252/184; 423/228
(58) Field of Classification Search
CPC combination set(s) only.
See application file for complete search history.

(56) References Cited

U.S. PATENT DOCUMENTS

| 1,882,258 A | 10/1932 | Randel |
| 2,516,625 A | 7/1950 | Haury |
| 2,601,673 A | 6/1952 | McMillan et al. |
| 2,802,344 A | 8/1957 | Witherell |
| 3,276,217 A | 10/1966 | Bourne et al. |
| 3,580,759 A | 5/1971 | Albertson et al. |
| 3,609,087 A | 9/1971 | Chi et al. |
| 4,106,904 A | 8/1978 | Oude Alink et al. |
| 4,112,051 A | 9/1978 | Sartori et al. |
| 4,152,900 A | 5/1979 | Chopra et al. |
| 4,152,901 A | 5/1979 | Munters |
| 4,201,721 A | 5/1980 | Hallgren |
| 4,251,494 A | 2/1981 | Say |
| 4,360,363 A | 11/1982 | Ferrin et al. |
| 4,466,915 A | 8/1984 | Lai |
| 4,701,530 A | 10/1987 | Swearingen et al. |
| 4,714,597 A | 12/1987 | Trevino |
| 5,016,445 A | 5/1991 | Wehr |
| 5,126,189 A | 6/1992 | Tanny et al. |
| 5,186,010 A | 2/1993 | Wehr |
| 5,303,565 A | 4/1994 | Pravda |
| 5,873,260 A | 2/1999 | Linhardt et al. |
| 6,117,963 A | 9/2000 | Boinowitz et al. |
| 6,130,347 A | 10/2000 | Julius et al. |
| 6,155,057 A | 12/2000 | Angell et al. |
| 6,184,433 B1 | 2/2001 | Harada et al. |
| 6,680,047 B2 | 1/2004 | Klaveness et al. |
| 6,727,015 B1 | 4/2004 | Putter et al. |
| 7,419,646 B2 | 9/2008 | Cadours et al. |
| 7,435,318 B2 | 10/2008 | Arlt et al. |
| 7,827,820 B2 | 11/2010 | Weimer et al. |
| 8,069,687 B2 | 12/2011 | Jork et al. |

(Continued)

FOREIGN PATENT DOCUMENTS

| DE | 400 488 | 8/1924 |
| DE | 633 146 | 7/1936 |

(Continued)

OTHER PUBLICATIONS

English language abstract for WO 2012/062830 and published on May 18, 2012.
English abstract for WO 2012/062656 and published on May 18, 2012.
English abstract for WO 2012/168067 and published on Dec. 13, 2012.
English language abstract for WO 2012/168094 and published on Dec. 13, 2012.
English abstract for WO 2012/168095 and published on Dec. 13, 2012.
English abstract for WO 2013/050230 and published on Apr. 11, 2013.
English abstract for WO 2013/050242 and published on Apr. 11, 2013.

(Continued)

*Primary Examiner* — Duane Smith
*Assistant Examiner* — Cabrena Holecek
(74) *Attorney, Agent, or Firm* — Law Office of: Michael A. Sanzo, LLC

(57) ABSTRACT

$CO_2$ is absorbed from a gas mixture by contacting the gas mixture with an absorption medium which comprises at least water as solvent and at least one amine of formula (I)

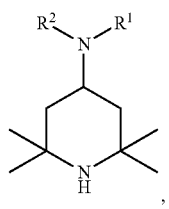

(I)

where $R^1$ is an aliphatic radical, having 2 to 6 carbon atoms and at least one amino group, and $R^2$ is hydrogen, a $C_{1-4}$ alkyl radical or a radical $R^1$.

20 Claims, No Drawings

(56) References Cited

U.S. PATENT DOCUMENTS

| | | | |
|---|---|---|---|
| 8,318,117 | B2 | 11/2012 | Lichtfers et al. |
| 8,357,344 | B2 | 1/2013 | Bouillon et al. |
| 8,500,867 | B2 | 8/2013 | Seiler et al. |
| 8,500,892 | B2 | 8/2013 | Seiler et al. |
| 8,506,839 | B2 | 8/2013 | Shiflett et al. |
| 8,623,123 | B2 | 1/2014 | Seiler et al. |
| 2004/0133058 | A1 | 7/2004 | Arlt et al. |
| 2005/0070717 | A1 | 3/2005 | Wasserscheid et al. |
| 2005/0129598 | A1 | 6/2005 | Chinn |
| 2005/0202967 | A1* | 9/2005 | Hoefer et al. ............... 502/401 |
| 2005/0245769 | A1 | 11/2005 | Kohler et al. |
| 2006/0104877 | A1* | 5/2006 | Cadours et al. ............. 423/226 |
| 2006/0150665 | A1 | 7/2006 | Weimer et al. |
| 2006/0197053 | A1 | 9/2006 | Shiflett et al. |
| 2006/0251961 | A1 | 11/2006 | Olbert et al. |
| 2007/0144186 | A1 | 6/2007 | Shiflett et al. |
| 2007/0264180 | A1 | 11/2007 | Carrette et al. |
| 2007/0286783 | A1 | 12/2007 | Carrette et al. |
| 2008/0028777 | A1 | 2/2008 | Boesmann et al. |
| 2008/0283383 | A1 | 11/2008 | Ruffert et al. |
| 2009/0029121 | A1 | 1/2009 | Hammermann et al. |
| 2009/0199709 | A1* | 8/2009 | Rojey et al. ................. 95/46 |
| 2010/0011958 | A1 | 1/2010 | Cadours et al. |
| 2010/0029519 | A1 | 2/2010 | Schwab et al. |
| 2010/0095703 | A1 | 4/2010 | Jork et al. |
| 2010/0104490 | A1 | 4/2010 | Bouillon et al. |
| 2010/0288126 | A1 | 11/2010 | Agar et al. |
| 2010/0326126 | A1 | 12/2010 | Seiler |
| 2011/0000236 | A1 | 1/2011 | Seiler |
| 2011/0081287 | A1 | 4/2011 | Bouillon et al. |
| 2012/0011886 | A1 | 1/2012 | Shiflett et al. |
| 2012/0017762 | A1 | 1/2012 | Seiler |
| 2012/0080644 | A1 | 4/2012 | Seiler |
| 2012/0247144 | A1 | 10/2012 | Seiler |
| 2012/0308458 | A1 | 12/2012 | Seiler |
| 2013/0031930 | A1 | 2/2013 | Seiler |
| 2013/0031931 | A1 | 2/2013 | Seiler |
| 2013/0118350 | A1 | 5/2013 | Rolker |
| 2013/0219949 | A1 | 8/2013 | Seiler et al. |

FOREIGN PATENT DOCUMENTS

| | | | |
|---|---|---|---|
| DE | 36 23 680 A1 | 1/1988 | |
| DE | 266 799 A1 | 4/1989 | |
| DE | 195 11 709 | 10/1996 | |
| DE | 103 33 546 | 2/2005 | |
| DE | 10 2004 053 167 | 5/2006 | |
| DE | 10 2005 013 030 | 9/2006 | |
| DE | 10 2006 036228 A1 | 2/2008 | |
| DE | 10 2009 000 543 | 8/2010 | |
| EP | 0 033 529 A1 | 1/1981 | |
| EP | 0 302 020 | 2/1989 | |
| EP | 302020 A2 * | 2/1989 | ........... C07D 211/58 |
| EP | 2 087 930 A1 | 8/2009 | |
| EP | 2 093 278 A1 | 8/2009 | |
| FR | 2 898 284 A1 | 9/2007 | |
| FR | 2 900 841 A1 | 11/2007 | |
| FR | 2 900 842 A1 | 11/2007 | |
| JP | 61-129019 | 6/1986 | |
| JP | 62-73055 | 4/1987 | |
| JP | 1-134180 | 5/1989 | |
| JP | 2-298767 | 12/1990 | |
| JP | 4-268176 | 9/1992 | |
| JP | 6-307730 | 11/1994 | |
| JP | 7-167521 | 7/1995 | |
| JP | 2001-219164 | 8/2001 | |
| JP | 2004-44945 | 2/2004 | |
| JP | 2006-239516 | 9/2006 | |
| WO | WO 93/13367 | 7/1993 | |
| WO | WO 00/61698 A1 | 10/2000 | |
| WO | WO 02/074718 | 9/2002 | |
| WO | WO 03/074494 | 9/2003 | |
| WO | WO 2004/104496 | 12/2004 | |
| WO | WO 2005/113702 | 12/2005 | |
| WO | WO 2006/084262 | 8/2006 | |
| WO | WO 2006/134015 | 12/2006 | |
| WO | WO 2007/070607 | 6/2007 | |
| WO | WO 2008/015217 | 2/2008 | |
| WO | WO 2009/097930 | 8/2009 | |
| WO | WO 2009/098155 | 8/2009 | |
| WO | WO 2009/156271 | 12/2009 | |
| WO | WO 2010/089257 | 8/2010 | |
| WO | WO 2012/062656 | 5/2012 | |
| WO | WO 2012/062830 | 5/2012 | |
| WO | WO 2012/168067 | 12/2012 | |
| WO | WO 2012/168094 | 12/2012 | |
| WO | WO 2012/168095 | 12/2012 | |
| WO | WO 2013/050230 | 4/2013 | |
| WO | WO 2013/050242 | 4/2013 | |

OTHER PUBLICATIONS

English language translation of the International Search Report for corresponding international application PCT/EP2011/069787, filed Nov. 10, 2011.

English language translation of the Written Opinion of the International Searching Authority for corresponding application PCT/EP2011/069787, filed Nov. 10, 2011.

English language translation of the International Preliminary Report on Patentability for corresponding international application PCT/EP2011/069787 with Letter from PCT applicant dated Mar. 27, 2012 and amended claims attached, application filed on Nov. 10, 2011.

Brennecke, et al., "Ionic Liquids. Innovative Fluids for Chemical Processing," *AIChE Journal* 47(11):2384-2389 (2001).

Chua, et al., "Improved Thermodynamic Property Fields of LiBr—$H_2O$ Solution," *International Journal of Refrigeration* 23:412-429 (2000).

De Lucas, et al., "Vapor Pressures, Densities, and Viscosities of the (Water + Lithium Bromide + Lithium Formate) System and (Water + Lithium Bromide + Potassium Formate) System," *Journal of Chemical and Engineering Data, American Chemical Society*, US 48(1):18-22 (2003).

De Lucas, et al., "Absorption of Water Vapor into Working Fluids for Absorption Refrigeration Systems," *Industrial & Engineering Chemistry Research, American Chemical Society*, US 46(1):345-350 (2007).

Domanska, et al., Solubility of 1-Alkyl-3-ethylimidazolium-Based Ionic Liquids in Water and 1-Octanol, *J. Chem. Eng. Data* 53:1126-1132 (Apr. 2008).

Galán, et al., "Solvent Properties of Functionalized Ionic Liquids for $CO_2$ Absorption," *IChemE* 85(Al):31-39 (2007).

Glebov, et al., "Experimental Study of Heat Transfer Additive Influence on the Absorption Chiller Performance," *International Journal of Refrigeration* 25:538-545 (2002).

Kim, et al., "Surface tension and viscosity of 1-butyl-3-methylimidazolium iodide and 1-butyl-3-methylimidazolium tetrafluoroborate, and solubility of lithium bromide+1-butyl-3-methylimidazolium bromide in water," *Korean J. Chem. Eng.* 23(1):113-116 (2006).

Kim, et al., "Performance Evaluation of Absorption Chiller Using $LiBr + H_2N(CH_2)_2OH + H_2O$, $LiBr + HO(CH_2)_3OH + H_2O$, and $LiBr + (HOCH_2CH_2NH + H_2O$ as Working Fluids," *Applied Thermal Engineering* 19:217-225 (1999).

Kim, et al., "Refractive Index and Heat Capacity of 1-Butyl-3-Methylimidazolium Bromide and 1-Butyl-3-Methylimidazolium Tetrafluoroborate, and Vapor Pressure of Binary Systems for 1-Butyl-3-Methylimidazolium Tetrafluoroborate—Trifluoroethanol," *Fluid Phase Equilibria* 218:215-220 (2004).

Li, et al., "Correlation and Prediction of the Solubility of $CO_2$ and $H_2S$ in an Aqueous Solution of 2-Piperidineethanol and Sulfolane," *Ind. Eng. Chem. Res.* 37:3098-3104 (1998).

Liu, et al., The physical properties of aqueous solution of room-temperature ionic liquids based on imidazolium:Database and Evaluation, *J. Mol. Liquids* 140:68-72 (Jan. 2008).

Mitsubishi Heavy Industries, Ltd., "Flue Gas $CO_2$ Recovery Technology and Its Application to EOR: an Effective Strategy for Addressing the Issues of Global Warming and Peaking Oil Supply," vol. 44, p. 20-23 (2007).

(56) References Cited

OTHER PUBLICATIONS

English counterpart of document C42, Mitsubishi Heavy Industries, Ltd., "Flue Gas $CO_2$ Recovery Technology and Its Application to EOR: an Effective Strategy for Addressing the Issues of Global Warming and Peaking Oil Supply," vol. 44, p. 20-23 (2007).
Rolker, et al., "Abtrennung von Kohlendioxid aus Rauchgasen mittels Absorption," *Chemie Ingenieur Technik 78*:416-424 (2006).
Wasserscheid, et al., "Ionische Flüssigkeiten—neue "Lösungen" für die Übergangsmetall-katalyse," *Angewandte Chemie 112*(21):3926-3945 (2000).
Wasserscheid, et al., "Ionic Liquids—New "Solutions" for Transition Metal Catalysis," *Angew. Chem. Int. Ed. 39*:3772-3789 (2000).
Wu, et al., "Novel Ionic Liquid Thermal Storage for Solar Thermal Electric Power Systems," *Proceeding of Solar Forum. Solar Energy: The Power to Choose* Apr. 21-25, 2001.
Yoon, et al., "Cycle Analysis of Air-Cooled Absorption Chiller Using a New Working Solution," *Energy 24*:795-809 (1999).
Ziiang, et al., "Screening of ionic Liquids to Capture CO2 by COSMO-RS and Experiments," *AIChE Journal 54*(10):2171-2728 (Oct. 2008).
Zhou, The Vapor Surfactant Theory of Absorption and Condensation Enhancement, *Proc. Int. Sorption Heat Pump Conference*, Sep. 24-27, 2002.
Ziegler, et al., "Heat-Transfer Enhancement by Additives," *International Journal of Refrigeration 19*:301-309 (1996).
Ziegler, et al., "Multi-effect absorption chillers," *Rev. Int. Froid 16*(5):301-311 (1993).
Ziegler, et al., "Recent developments and future prospects of sorption heat pump systems," *Int. J. Therm. Sci. 38*:191-208 (1999).
English language translation of abstract for Rolker in 2006.
U.S. Appl. No. 13/883,573, filed May 5, 2013, Seiler.
U.S. Appl. No. 13/910,014, filed Jun. 4, 2013, Seiler.
English language abstract for JP 6-307730 and published on Nov. 1, 1994.
English language abstract for JP 2006-239516 and published on Sep. 14, 2006.
Perez-Blanco, "A Model of an Ammonia-Water Falling Film Absorber," ASHRAE Transactions vol. 94, pp. 467-483, 1988; (Presented at the 1988 winter meeting in Dallas Texas of the American Society of Heating, Refrigerating and Air-Conditioning Engineers, Inc).
Notice of Allowance for co-pending U.S. Appl. No. 13/910,014, mailed Sep. 6, 2013.
English language abstract for JP 1-134180 and published on May 26, 1989.
English language abstract for JP 2001-219164 and published on Aug. 14, 2001.
English language abstract for JP 2004-44945 and published on Feb. 12, 2004.
Office Action mailed Aug. 19, 2013 for co-pending U.S. Appl. No. 13/375,822.
Response to Office Action for co-pending U.S. Appl. No. 13/375,822, filed Sep. 19, 2013.
English abstract for DD 266 799 A1 and published on Apr. 12, 1989.
English text for DE 400 488 and published on Aug. 11, 1924.
English text for DE 633 146 and published on Jul. 20, 1936.
English abstract for DE 36 23 680 and published on Jan. 14, 1988.
English abstract for DE 195 11 709 and published on Oct. 2, 1996.
English abstract for DE 103 33 546 and published on Feb. 17, 2005.
English abstract for DE 10 2004 053 167 and published on May 4, 2006.
English abstract for DE 10 2009 000 543 and published on Aug. 12, 2010.
English abstract for EP 0 033 529 A1 and published on Jan. 31, 1981.
English abstract for EP 2 087 930 A1 and published on Aug. 12, 2009.
English abstract for EP 2 093 278 A1 and published on Aug. 26, 2009.
English abstract for FR 2 900 841 A1 and published on Nov. 16, 2007.
English abstract for JP 61-129019 and published on Jun. 17, 1986.
English abstract for JP 2-298767 and published on Dec. 11, 1990.
English abstract for JP 4-268176 and published on Sep. 24, 1992.
English abstract for JP 7-167521 and published on Jul. 4, 1995.
English abstract for WO 93/13367 and published on Jul. 8, 1993.
English abstract for WO 2008/015217 and published on Feb. 7, 2008.
English abstract for WO 2009/098155 and published on Aug. 13, 2009.
Partial English language translation for JP 62-73055 and published on Apr. 3, 1987.
English language translation of JP 7-167521 published on Jul. 4, 1995.
Preliminary Amendment filed Dec. 6, 2013 for copending U.S. Appl. No. 14/124,347.
Preliminary Amendment filed Dec. 6, 2013 for copending U.S. Appl. No. 14/124,385.
Preliminary Amendment filed Dec. 6, 2013 for copending U.S. Appl. No. 14/124,472.
U.S. Appl. No. 14/124,347, filed Dec. 6, 2013, Rolker.
U.S. Appl. No. 14/124,385, filed Dec. 6, 2013, Rolker.
U.S. Appl. No. 14/124,472, filed Dec. 6, 2013, Rolker.

\* cited by examiner

AMINE-CONTAINING ABSORPTION MEDIUM, PROCESS AND APPARATUS FOR ABSORPTION OF ACIDIC GASES FROM GAS MIXTURES

CROSS REFERENCE TO RELATED APPLICATIONS

The present application is US national stage of international application PCT/EP2011/069787, which had an international filing date of Nov. 10, 2011, and which was published in German under PCT Article 21(2) on May 18, 2012. Priority is claimed to German application DE 10 2010 043 838.3, filed on Nov. 12, 2010 and to German application DE 10 2011 077 377.0, filed on Jun. 10, 2011.

The invention describes a process for absorption of acid gases from a gas mixture, and also absorption media and a device for carrying out this process.

In numerous industrial and chemical processes, gas streams occur which have an unwanted content of $CO_2$ and/or other acid gases, and content thereof must be minimized or eliminated for further processing or transport.

These gas streams are, for example, natural gas, synthesis gas from heavy oil, refinery gas or liquefied hydrocarbon streams. Reaction gases which are formed in the partial oxidation of organic materials, such as, for example, coal or petroleum, can also contain $CO_2$ and/or other acid gases. Also in the case of biogases, the content of $CO_2$ and/or acid gases is frequently unwanted, which biogases can be formed from fermentable biomass-containing residual materials such as, for example, sewage sludge, biowaste, food residues, manures (liquid manure, dung), plant parts and also cultivated energy plants. The situation is similar with exhaust gases from combustion processes, such as, for example, flue gases from power plant processes. The content of $CO_2$ and/or acid gases from these various gas streams must be minimized for most varied reasons. In addition to reducing the emission of carbon dioxide which is considered to be the principle cause of what is termed the greenhouse effect, acid gases are frequently catalyst poisons in secondary processes, contribute to corrosion or decrease the calorific value (e.g. in the case of natural gas). A further aspect is that carbon dioxide is required as a starting material for some processes.

On an industrial scale, aqueous solutions of alkanolamines are usually employed as absorption medium for absorbing $CO_2$ from a gas mixture. The loaded absorption medium is regenerated by warming, expanding to a lower pressure or stripping, with the carbon dioxide being desorbed. After the regeneration process, the absorption medium can be reused. These processes are described, for example, in Rolker, J.; Arlt, W.; "Abtrennung von Kohlendioxid aus Rauchgasen mittels Absorption" [Separation of carbon dioxide from flue gases by absorption] in Chemie Ingenieur Technik 2006, 78, pages 416 to 424, and also in Kohl, A. L.; Nielsen, R. B., "Gas Purification", 5th edition, Gulf Publishing, Houston 1997.

These processes have the disadvantage that a relatively high amount of energy is required for separating $CO_2$ by absorption and subsequent desorption and that in the desorption only part of the adsorbed $CO_2$ is desorbed again, and so the proportion of alkanolamine used for absorbing $CO_2$ is low in a cycle of absorption and desorption. Furthermore, the absorption media used are highly corrosive and are subject to an interfering oxidative degradation in the absorption of $CO_2$ from oxygen-containing gas mixtures.

U.S. Pat. No. 7,419,646 describes a process for deacidifying exhaust gases in which an absorption medium is used which forms two separable phases upon absorption of the acid gas. 4-Amino-2,2,6,6-tetramethylpiperidine is cited, inter alia, in column 6 as a reactive compound for absorbing an acid gas. The process of U.S. Pat. No. 7,419,646 has the disadvantage that additional apparatus is required for separating the two phases which arise in the absorption.

DD 266 799 describes a process for purifying 4-amino-2,2,6,6-tetramethylpiperidine, in which $CO_2$ is introduced into a solution of 4-amino-2,2,6,6-tetramethylpiperidine in water and acetone and the precipitated salt is decomposed back to $CO_2$ and 4-amino-2,2,6,6-tetramethylpiperidine by heating it to 90 to 200° C.

WO 2010/089257 describes an absorption medium for absorbing $CO_2$ from a gas mixture, the absorption medium comprising water and at least one 4-(dialkylamino)-2,2,6,6-tetramethylpiperidine or 4-amino-2,2,6,6-tetramethylpiperidine. The use of 4-amino-2,2,6,6-tetramethylpiperidine frequently has the disadvantage that these processes are distinguished by relatively small $CO_2$ uptakes, caused by a relatively large mass flow of absorption medium that has to be pumped in the process and also regenerated again in the desorber.

WO 2009/156271 describes an absorption medium for absorbing acid gases from fluid streams, in particular from flue gases. For this purpose the absorption medium comprises an oligoamine and a primary or secondary alkanolamine. 4-Amino-2,2,6,6-tetramethylpiperidine can be added to the absorption medium as activator. The primary amines generally have high enthalpies of absorption, causing higher evaporator outputs in the desorption.

WO 2008/015217 describes a process for separating $CO_2$ from gas mixtures and also a corresponding device for this purpose. For this purpose, an absorbent medium having at least one secondary and/or at least tertiary amine is used, and as secondary amine, inter alia, 2,2,6,6-tetramethylpiperidine is listed. Here also, owing to relatively small $CO_2$ uptakes, relatively large mass flow rates of absorption medium need to be pumped in the process, which also must be regenerated again in the desorber. In addition, there is the risk that precipitation can occur after the absorption.

The Institut Francais du Petrole, in the publications US 2009/0199709, FR 2900841 and US 2007/0286783, describes an absorption medium which comprises, inter alia, 4-amino-2,2,6,6-tetramethylpiperidine and/or 1,2,2,6,6-pentamethyl-4-piperidine as amine. The 4-amino-2,2,6,6-tetramethylpiperidine can also be added as activator to the absorption medium. Here, the same disadvantages result as have already been indicated for WO 2010/089257.

The object of the present invention was therefore to provide an improved and thereby more economic process.

Surprisingly, a process has been found for absorption of acid gases from a gas mixture by contacting the gas mixture with an absorption medium, which is characterized in that the absorption medium comprises an amine (A) of the formula (I). The absorption medium according to the invention is distinguished from processes according to the prior art by its improved capacity for binding acid gases, in particular $CO_2$, so that overall a higher $CO_2$ uptake can be achieved. This offers the opportunity that the plant components in the process according to the invention may be dimensioned smaller. Thus for example, pumps, containers, pipes and absorption or desorption columns having a smaller diameter can be used in the process according to the invention. Owing to the properties of the absorption medium according to the invention, smaller amounts of absorption medium can also be used in the process according to the invention. Therefore, the buffer tank components can also be dimensioned smaller. Owing to the reduced amounts of absorption medium used, the energy consumption can also be reduced, since less energy is necessary for the process step of desorption.

In addition, the energy to be applied for elimination of the absorbed $CO_2$ is lower than according to the prior art. Furthermore, a synergist effect could be observed completely unexpectedly when an absorption medium is used which comprises both an amine (A) of formula (I) and an amine (B) of formula (III). The $CO_2$ uptake measured in this case is greater than the arithmetic mean of the measured $CO_2$ uptakes for the absorption media which each have only one of these amines.

The invention therefore relates to a process for absorption of an acid gas from a gas mixture by contacting the gas mixture with an absorption medium, which is characterized in that an absorption medium is used which comprises at least water as solvent and at least one amine (A) of formula (I)

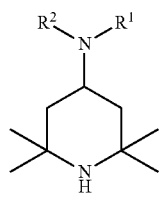
(I)

where
- $R^1$=aliphatic radical having 2 to 6 carbon atoms and having at least one amino group,
- $R^2$=hydrogen, a $C_{1-4}$ alkyl group or a radical $R^1$.

In addition, the invention relates to an absorption medium which comprises at least water as solvent and at least one amine (A) of formula (I), and to a device for separating acid gases from a gas mixture, said device comprising an absorption unit, a desorption unit and a circulating absorption medium, which is characterized in that said device comprises an absorption medium according to the invention.

The process according to the invention for absorption of an acid gas from a gas mixture by contacting the gas mixture with an absorption medium is distinguished in that an absorption medium is used which comprises at least water as solvent and at least one amine (A) of formula (I)

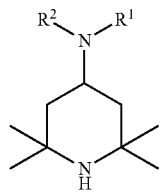
(I)

where
- $R^1$=aliphatic radical having 2 to 6 carbon atoms and having at least one amino group,
- $R^2$=hydrogen, $C_{1-4}$ alkyl group or radical $R^1$.

Preferably, the absorption medium used comprises an amine (A) of formula (I) in which $R^2$ is hydrogen.

Preferably, the absorption medium used comprises an amine (A) of formula (II)

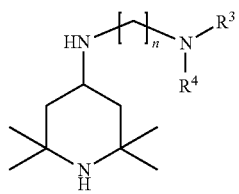
(II)

where
- $R^3$=hydrogen or $C_{1-4}$ alkyl group, preferably hydrogen or methyl group, particularly preferably methyl group,
- $R^4$=$C_{1-4}$ alkyl group, preferably $C_{1-2}$ alkyl group, particularly preferably methyl group,
- n=2 to 4, preferably 2 to 3 and particularly preferably 3.

Most preferably, the absorption medium used comprises an amine (A) of the formula (II) where $R^3$, $R^4$=methyl and n=3.

The alkyl groups, in the context of this invention, can be substituted or unsubstituted, in addition $C_{3-4}$ alkyl groups can be linear or branched.

In addition to amine (A), the absorption medium used in the process according to the invention, can comprise a further amine (B) of formula (III)

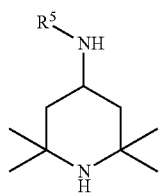
(III)

where
- $R^5$=$C_{1-6}$ alkyl group, preferably $C_{3-5}$ alkyl group, and particularly preferably butyl group.

The alkyl groups, in the context of this invention, can be substituted or unsubstituted, in addition the $C_{3-6}$ alkyl groups can be linear or branched. The substituent of the type $R^5$ is preferably unsubstituted, preferably an unsubstituted butyl group, and particularly preferably an unsubstituted n-butyl group.

The absorption medium used in the process according to the invention comprises at least water as solvent. The absorption medium used, however, can also contain a further physical solvent (C). This is advantageous to further increase the loading of the absorption medium with the acid gases at a high partial pressure of the acid gas, in particular of $CO_2$. In this manner, the mass flow rate of absorption medium can be further reduced. At the same time, an energetically more favourable regeneration may be carried out, in that it is possible to perform regeneration not only thermally, but alternatively or in supplementation, also by a flash (pressure reduction).

The choice of the solvent (C) and the content of the solvent (C) in the absorption medium used is based on various criteria such as, for example, the composition of the gas mixture which is to be purified (e.g. fractions of acidic components, fraction of hydrocarbons), the prevailing partial pressure of the acid gases to be removed, such as, for example, $CO_2$, and also the specifications to be met for the gas purified with the process according to the invention.

In a particular embodiment of the process according to the invention, the content of the solvent (C), based on the absorption medium used, is from 20 to 40% by weight. This embodiment is suitable in particular when the partial pressure of the acid gas is particularly high, preferably at least 20 bar, and the requirements for the purified gas are likewise high, preferably when the partial pressure of the acid gas in the purified gas should be a maximum of 10 mbar. This way the loading of the absorption medium with the acid gases can be further increased, which in turn leads to lower mass flow rates of absorption medium. The fraction of the amine (A) is preferably 10 to 25% by weight, and the fraction of the amine (B) is preferably 5 to 15% by weight, based on the absorption medium used. In this manner, purification of a gas is possible with the aim of achieving a partial pressure of the acid gas that is as low as possible. In addition, the absorption medium mass flow rate used decreases. An energetically more favourable regeneration of the solvent can be achieved by the reduced mass flow rate and the fraction of the physical solvent, since some of the acid gas can be separated via a flash. In addition, regeneration can further be performed by a desorber in order to deplete the solvent further in acid gases, but at a reduced steam requirement in the evaporator of the desorber.

As further solvent (C), the absorption medium used in the process according to the invention can comprise the physical solvents known from gas scrubbing such as, for example, sulfolane, propylene carbonate, N-alkylated pyrrolidones (e.g. N-methyl-2-pyrrolidones) and N-alkylated piperidones, dialkyl ethers of polyethylene glycol and mixtures thereof, aliphatic acid amides (e.g. N-formylmorpholine or N-acetyl-morpholine), methyl cyanoacetate.

The further solvent (C) can also have the action of a solubilizer in the process according to the invention. The temperature at which a phase separation of the absorption medium loaded with acid gases takes place can be increased by the addition of a further solvent (C). This simplifies, in particular, the subsequent desorption, since here frequently a temperature increase is also employed, and therefore no special process measures are necessary for a multiphase system. With an absorption medium which comprises exclusively water and an amine (A) of formula (I) the temperature at which the phase separation starts is higher than with an absorption medium which comprises exclusively water and an amine (B) of formula (III). The process according to the invention, therefore, has the advantage that the acid gases can be desorbed, or the absorption medium can be regenerated, at higher temperatures without a phase separation occurring. Depending on requirements of use, a favoured regeneration process can be selected by the appropriately selected formulation of the absorption medium according to defined proportions of the amines (A), (B) and the solvent (C). If, e.g., a high degree of depletion of the acid gases must be achieved and existing plant equipment with a desorber column shall be used, a composition can be selected in which the absorption medium loaded with acid gases does not segregate.

In addition, the composition of the absorption medium can be selected in such a manner that separation of the absorption medium loaded with acid gases into an aqueous phase and an organic phase occurs at a temperature increase. This case can offer further advantages in regeneration, since an energetically more favourable flash is already sufficient and the absorption medium loaded with acid gases can be freed from acid gas, in particular $CO_2$, in a flash at moderate temperature elevation.

Preferably, an absorption medium is used in the process according to the invention which comprises 60 to 80% by weight of water and optionally solvent (C),
1 to 40% by weight of the amine (A) and
0 to 39% by weight of the amine (B).
More preferably, the absorption medium used comprises
65 to 75% by weight of water and optionally solvent (C),
10 to 20% by weight of the amine (A) and
25 to 5% by weight of the amine (B).
Most preferably, the absorption medium used comprises
65 to 75% by weight of water,
10 to 20% by weight of the amine (A) of formula (II) where $R^3$, $R^4$=methyl and n=3 and
25 to 5% by weight of amine (B) of the formula (III) where $R^5$=n-propyl or n-butyl.

Using this composition, a phase separation temperature in the range from 85 to 110° C. can be set for the absorption medium loaded with acid gases.

The absorption medium used in the process according to the invention can also comprise performance additives, such as, for example, corrosion inhibitors, activators, wetting-promoting additives and/or defoamers.

In the process according to the invention, all substances, which are known to those skilled in the art as suitable corrosion inhibitors for processes for absorbing $CO_2$ using alkanolamines, can be used as corrosion inhibitors, in particular the corrosion inhibitors described in U.S. Pat. No. 4,714,597.

The amount of corrosion inhibitors which the absorption medium used in the process according to the invention preferably comprises is markedly reduced compared with processes according to the prior art, since the absorption medium used in the process according to the invention is markedly less corrosive towards metallic materials than the monoethanolamine frequently used according to the prior art.

Preferably one or more surfactants from the group of the non-ionic surfactants, zwitterionic surfactants and cationic surfactants are used as wetting-promoting additive.

Suitable non-ionic surfactants are alkylaminealkoxylates, amidoamines, alkanolamides, alkylphosphine oxides, N-alkyl glucamides, alkyl glucosides, bile acids, alkyl alkoxylates, sorbitan esters, sorbitan ester ethoxylates, fatty alcohols, fatty acid ethoxylates, ester ethoxylates and polyether siloxanes.

Suitable zwitterionic surfactants are betaines, alkylglycines, sultaines, amphopropionates, amphoacetates, tertiary amine oxides and silicobetaines.

Suitable cationic surfactants are quaternary ammonium salts bearing one or two substituents having 8 to 20 carbon atoms, in particular corresponding tetraalkylammonium salts, alkylpyridinium salts, ester quats, diamidoamine quats, imidazolinium quats, alkoxyalkyl quats, benzyl quats and silicone quats.

In a preferred embodiment, the wetting-promoting additive comprises one or more nonionic surfactants of general formula $R(OCH_2CHR')_mOH$ having m from 4 to 40, where R is an alkyl radical having 8 to 20 carbon atoms, an alkylaryl radical having 8 to 20 carbon atoms or a polypropylene oxide radical having 3 to 40 propylene oxide units and R' is methyl, or preferably hydrogen.

In a further preferred embodiment, the wetting-promoting additive comprises a polyether-polysiloxane copolymer which contains more than 10% by weight of $[Si(CH_3)_2O]$ units and more than 10% by weight of $[CH_2CHR''—O]$ units in which R'' is hydrogen or methyl. Particular preference is given to polyether-polysiloxane copolymers of the general formulae (IV) to (VI):

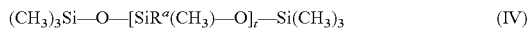

(IV)

(V)

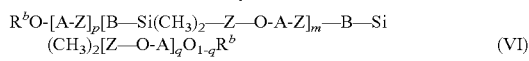

$$R^b\text{O-[A-Z]}_p\text{[B—Si(CH}_3)_2\text{—Z—O-A-Z]}_m\text{—B—Si} \\ \text{(CH}_3)_2\text{[Z—O-A]}_q\text{O}_{1-q}R^b \quad (VI)$$

where
- A is a divalent radical of the formula —[CH$_2$CHR$^c$—O]$_r$—,
- B is a divalent radical of the formula —[Si(CH$_3$)$_2$—O]$_s$—,
- Z is a divalent linear or branched alkylene radical having 2 to 20 carbon atoms, and preferably —(CH$_2$)$_3$—,
- t=1 to 30,
- m=2 to 100,
- p, q=0 or 1,
- r=2 to 100,
- s=2 to 100,
- R$^a$ from 1 to 5 of the radicals R$^a$ are radicals of the general formula —Z—O-A-R$^b$— and the remaining radicals R$^a$ are methyl,
- R$^b$ is hydrogen, an alkyl radical or an aliphatic or olefinic acyl radical having 1 to 20 carbon atoms and
- R$^c$ is hydrogen or methyl.

The wetting-promoting additives are already known to those skilled in the art from the prior art as additives for aqueous solutions and can be produced according to processes known from the prior art.

The absorption medium used in the process according to the invention can comprise what are termed activators. By using activators, the desired separation effect can be further improved. Preferably, primary or secondary amines are used as activators in the process according to the invention, which activators do not have a structure according to formulae (I) to (III). Amines which are suitable for this purpose are preferably amines which have rapid kinetics with respect to binding acid gases, in particular CO$_2$. Preferably, activators selected from monoethanolamine, piperazine and 3-(methylamino)-propylamine are used. The absorption medium comprises in the process according to the invention preferably from 0 to 20% by weight of the activators.

Acid gases are meant to be compounds which under the prevailing conditions are in the gaseous state in the gas mixture to be purified and have a pH below 7 in aqueous solution. Typical acid gases are, for example, carbon dioxide (CO$_2$), hydrogen sulphide (H$_2$S), sulphur dioxide (SO$_2$), carbonyl sulphide (COS), carbon disulphide (CS$_2$), hydrogen cyanide (HCN) and mercaptans (RSH). The process according to the invention is preferably used for removing CO$_2$ from a gas mixture.

With the process according to the invention it is possible to purify gas mixtures selected from natural gas, synthesis gas, combustion exhaust gases; exhaust gases from biological processes such as composting processes, fermentations or sewage treatment plants; exhaust gases from calcination processes such as lime burning and cement production; residual gases from blast-furnace processes of iron production; and also residual gases from chemical processes, and also exhaust gases from carbon black production or hydrogen production by steam reforming, wherein the acid gases, in particular CO$_2$, are removed.

The process according to the invention is suitable preferably for removing CO$_2$ from natural gas, synthesis gas, flue gases or a combustion exhaust gas, more preferably for removing CO$_2$ from natural gas, synthesis gas or a combustion exhaust gas.

Particularly preferably, the gas mixture used in the process according to the invention is natural gas or synthesis gas.

The residual CO$_2$ content of the gas purified with the process according to the invention is preferably a maximum of 2% by weight for pipeline natural gas, preferably a maximum of 50 ppm for liquid natural gas and preferably a maximum of 500 ppm for synthesis gas.

For the process according to the invention, all apparatuses suitable for contacting a gas phase with a liquid phase can be used in order to contact the gas mixture with the absorption medium. Preferably, prior art gas scrubbers or absorption columns are used, for example membrane contactors, radial flow scrubbers, jet scrubbers, venturi scrubbers, rotary spray scrubbers, random packing columns, ordered packing columns and tray columns. Particularly preferably, absorption columns are used in countercurrent flow mode.

In the process according to the invention, the acid gases, in particular CO$_2$, are absorbed preferably at a temperature of the absorption medium in the range from 0 to 70° C., and more preferably 20 to 60° C. When an absorption column is used in countercurrent flow mode, the temperature of the absorption medium is particularly preferably 30 to 60° C. on entry into the column and 35 to 70° C. on exit from the column.

The total pressure of the gas mixture in the process according to the invention during the absorption process step is of lesser importance. However, it has turned out to be advantageous that the absorption of acid gases, in particular CO$_2$, is carried out at a total pressure of the gas mixture in the range from 0.8 to 50 bar, preferably in the range from 0.9 to 30 bar. In a particularly preferred embodiment, the absorption is carried out at a total pressure of the gas mixture in the range from 0.8 to 1.5 bar, in particular 0.9 to 1.1 bar. This particularly preferred embodiment is advisable in the absorption of CO$_2$ from the combustion exhaust gas of a power plant without compression of the combustion exhaust gas.

The partial pressure of the acid gas, in particular the CO$_2$, varies with the gas mixture to be purified by the process according to the invention. For instance, the partial pressure of the acid gases in the gas mixture to be purified is from 0.1 bar to 60 bar for natural gas, from 0.1 bar to 35 bar for synthesis gas and from 0.03 bar to 0.15 bar for flue gases from power plants.

In a particularly preferred embodiment of the process according to the invention, the partial pressure of the acid gas, in particular the CO$_2$, is from 0.1 bar to 20 bar.

In a further preferred embodiment of the process according to the invention, particularly high partial pressures of the acid gas, in particular the CO$_2$, are present in the gas mixture, in particular partial pressures of at least 15 bar. In this case, the proportion of the physical solvent (C) in the absorption medium is at least 30% by weight.

The absorption medium that is leaving the absorber and is loaded with the acid gas, in particular CO$_2$, can be single-phase or two-phase after the absorption process step. In the process according to the invention, however, temperature and pressure in the absorption process step and also the composition of the absorption medium are preferably selected in such a manner that the absorption medium, after absorption of the acid gas, in particular CO$_2$, is present as a single phase, i.e. the absorption of the acid gas in the absorption medium does not lead to precipitation of a solid or to formation of two liquid phases. This preferred embodiment of the process according to the invention therefore requires no additional apparatuses for phase separation and can be carried out in the devices known from the prior art for absorbing CO$_2$ with alkanolamines.

In a preferred embodiment of the process according to the invention, acid gas, in particular CO$_2$, absorbed in the absorption medium is desorbed again by increasing the temperature and/or by reducing the pressure and the absorption medium, after this desorption of the acid gas, in particular $CO_2$, is reused for absorbing acid gases. By such a cyclic process of absorption and desorption, the acid gases, in particular $CO_2$, can be entirely or partially separated from the gas mixture and obtained separately from other components of the gas mixture.

Alternatively or complementary to a temperature increase and/or pressure reduction, a desorption can also be carried out by stripping the absorption medium that is loaded with acid gases, in particular $CO_2$, with a gas, for example nitrogen or air. Desorption by stripping with a gas has the advantage that it requires less energy than a desorption in a desorption column.

If, in the desorption of the acid gases, water is also removed from the absorption medium, water may be added as necessary to the absorption medium before reuse for absorption.

All apparatuses which are known from the prior art for desorbing a gas from a liquid can be used for the desorption. Preferably, the desorption is carried out in a desorption column. Alternatively or complementary, the acid gases, in particular $CO_2$, can also be desorbed in one or more flash evaporation stages.

In a desorption by temperature increase, the acid gases, in particular $CO_2$, are preferably desorbed at a temperature of the absorption medium in the range from 50 to 200° C., more preferably 55 to 150° C., and particularly preferably from 60 to 100° C. The temperature during the desorption in this case is preferably at least 20° C., particularly preferably at least 50° C., above the temperature during the absorption.

During the desorption process step in the process according to the invention, the desorption of acid gases, in particular $CO_2$, by reducing the pressure is preferably carried out at a total pressure in the gas phase in the range from 0.01 to 10 bar, in particular 0.1 to 5 bar. Preferably, the desorption is carried out at a pressure of at least 1.5 bar, and particularly preferably of at least 2 bar.

In a desorption by increasing the temperature, the pressure during the desorption of the acid gases, in particular $CO_2$, can also be higher than during the absorption of the acid gases. In this embodiment, the pressure during the desorption of the acid gases is preferably up to 5 bar, particularly preferably up to 3 bar, above the pressure during the absorption of the acid gases. Using this embodiment, the acid gases separated from the gas mixture can be compressed to a higher pressure than that of the gas mixture without using mechanical energy.

In a preferred embodiment of the process according to the invention, the absorption medium loaded with acid gases is first freed from the acid gases by pressure reduction in one or more sequential flash evaporation stages and the still remaining proportion of acid gases is then removed in a desorption column by stripping, preferably with an inert gas, such as, for example, air or nitrogen. In the last flash evaporation stages the pressure can be lowered to 1 to 5 bar, preferably to 1 to 2 bar. This embodiment has the advantage that the temperature in the desorber can be selected so as to be lower, preferably from 60 to 100° C. In addition, the absorption medium can be effectively freed from the acid gases by the combination of pressure reductions and temperature elevation and is available for the next absorption of acid gases with virtually the same low $CO_2$ loading. In this manner, the amount of absorption medium in the overall process can be lowered.

In a further embodiment of the process according to the invention, a two-phase liquid system forms after the absorption depending on the temperature and the composition of the absorption medium. The desorption of the acid gases and/or regeneration of the absorption medium can in this case also be performed by a flash evaporation stage or by a plurality of sequential flash evaporation stages. In doing so, the temperature of the absorption medium is increased before the pressure reduction in the flash. In this manner the acid gases, such as, for example, $CO_2$, can be removed again from the absorption medium. This kind of regeneration is markedly more energetically favourable than the operation of a desorption column. In this case, it is advisable to take suitable measures upstream of the absorber in the further course of the process, in order to bring the absorption medium back into a homogeneous solution. For this purpose, inter alia, static mixers or tanks with a stirrer or recirculating pump are suitable.

After the absorption medium has been contacted with the gas mixture, it is preferably heated to a temperature at which a phase separation into an aqueous liquid phase and an organic liquid phase occurs, and acid gas is desorbed from the resultant two-phase mixture by stripping with an inert gas. A suitable inert gas in this case are all gases which do not participate in a reaction with the amines (A) and (B) under the desorption conditions, in particular nitrogen and air. Because of the low number of apparatuses and the low energy requirement, this embodiment has the advantage of low capital and operating costs.

In a further preferred embodiment of the process according to the invention, after the absorption medium has been contacted with the gas mixture, it is heated to a temperature at which a phase separation into an aqueous liquid phase and an organic liquid phase proceeds, and acid gas is desorbed from the aqueous liquid phase by reducing the pressure and/or supplying heat. The resultant liquid phase is combined with the organic liquid phase obtained in the phase separation and the combined liquid phases are again contacted as absorption medium with the gas mixture. In the separation of $CO_2$ from natural gas or synthesis gas, the heating of the loaded absorption medium and the phase separation are preferably carried out at a pressure at which $CO_2$ is not desorbed and $CO_2$ is desorbed only from the aqueous phase obtained in the phase separation. Thereby, the methane content in the desorbed $CO_2$ may be kept low in the separation of $CO_2$ from natural gas and the contents of hydrogen and CO in the desorbed $CO_2$ may be kept low in the separation of $CO_2$ from synthesis gas.

The amine-containing absorption medium according to the invention is distinguished in that it comprises at least water as solvent and at least one amine (A) of formula (I)

(I)

where
- $R^1$=aliphatic radical having 2 to 6 carbon atoms and having at least one amino group,
- $R^2$=hydrogen, $C_{1-4}$ alkyl group or radical $R^1$.

Preferably, the absorption medium according to the invention comprises an amine (A) of formula (I) where $R^2$ is hydrogen.

More preferably, the absorption medium according to the invention comprises an amine (A) of formula (II)

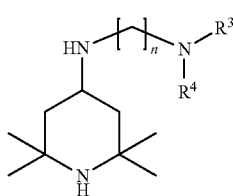

where
R³=hydrogen or C₁₋₄ alkyl group, preferably hydrogen or methyl group, particularly preferably methyl group,
R⁴=C₁₋₄ alkyl group, preferably C₁₋₂ alkyl group, particularly preferably methyl group,
n=2 to 4, preferably 2 to 3 and particularly preferably 3.

Most preferably, the absorption medium according to the invention comprises an amine (A) of the formula (II) where R³, R⁴=methyl and n=3.

The alkyl groups, in the context of this invention, can be substituted or unsubstituted, in addition, C₃₋₄ alkyl groups can be linear or branched.

In addition to amine (A) the absorption medium according to the invention can comprise a further amine (B) of formula (III)

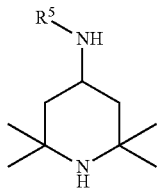

where
R⁵=C₁₋₆ alkyl group, preferably C₃₋₅ alkyl group, and particularly preferably butyl group.

The alkyl groups, in the context of this invention, can be substituted or unsubstituted, in addition the C₃₋₆ alkyl groups can be linear or branched. The substituent of the type R⁵ is preferably unsubstituted, preferably an unsubstituted butyl group, and particularly preferably an unsubstituted n-butyl group.

The absorption medium according to the invention comprises at least water as solvent. The absorption medium used, however, can also contain a further physical solvent (C). This is advantageous to further increase the loading of the absorption medium with the acid gases at a high partial pressure of the acid gas, in particular of CO₂. In this manner, the mass flow rate of absorption medium can be further reduced. At the same time, an energetically more favourable regeneration may be carried out, in that it is possible to perform regeneration not only thermally, but alternatively or in supplementation, also by a flash (pressure reduction).

The choice of the solvent (C) and also the content of the solvent (C) in the absorption medium according to the invention is based on various criteria such as, for example, composition of the gas mixture which is to be purified (e.g. fractions of acid components, fraction of hydrocarbons), the prevailing partial pressure of the acid gases to be removed, such as, for example, CO₂, and also the specifications to be met for the gas purified with the process according to the invention.

In a particular embodiment of the absorption medium according to the invention, the content of the solvent (C), based on the absorption medium used, is from 20 to 40% by weight. This embodiment is suitable in particular when the partial pressure of the acid gas is particularly high, preferably at least 20 bar, and the requirements for the purified gas are likewise high, preferably when the partial pressure of the acid gas in the purified gas should be a maximum of <10 mbar. This way the loading of the absorption medium with the acid gases can be further increased, which in turn leads to lower mass flow rates of absorption medium. The fraction of the amine (A) is preferably 10 to 25% by weight, and the fraction of the amine (B) is preferably 5 to 15% by weight, based on the absorption medium used. In this manner, purification of a gas is possible with the aim of achieving a partial pressure of the acid gas that is as low as possible.

As further solvent (C), the absorption medium according to the invention can comprise the physical solvents known from gas scrubbing such as, for example, sulfolane, propylene carbonate, N-alkylated pyrrolidones (e.g. N-methyl-2-pyrrolidones) and N-alkylated piperidones, dialkyl ethers of polyethylene glycol and mixtures thereof, aliphatic acid amides (e.g. N-formylmorpholine or N-acetylmorpholine), methyl cyanoacetate.

Preferably, the absorption medium according to the invention comprises
60 to 80% by weight of water and optionally solvent (C),
1 to 40% by weight of the amine (A) and
0 to 39% by weight of the amine (B).

More preferably, the absorption medium according to the invention comprises
65 to 75% by weight of water and optionally solvent (C),
10 to 20% by weight of the amine (A) and
25 to 5% by weight of the amine (B).

Most preferably, the absorption medium according to the invention comprises
65 to 75% by weight of water,
10 to 20% by weight of the amine (A) of formula (II) where R³, R⁴=methyl and n=3 and
25 to 5% by weight of amine (B) of the formula (III) where R⁵=n-propyl or n-butyl.

Using this composition, a phase separation temperature in the range from 85 to 110° C. can be set for the absorption medium loaded with acid gases.

The absorption medium according to the invention can also comprise performance additives, such as, for example, corrosion inhibitors, activators, wetting-promoting additives and/or defoamers.

As corrosion inhibitors, the absorption medium according to the invention can comprise all substances which are known to those skilled in the art as suitable corrosion inhibitors for processes for absorbing CO₂ using alkanolamines, in particular the corrosion inhibitors described in U.S. Pat. No. 4,714,597.

The amount of corrosion inhibitors in the absorption medium according to the invention is preferably markedly reduced compared with processes according to the prior art, since the absorption medium according to the invention is markedly less corrosive towards metallic materials than the monoethanolamine frequently used according to the prior art.

As wetting-promoting additive, the absorption medium according to the invention preferably comprises one or more surfactants from the group of the non-ionic surfactants, zwitterionic surfactants and cationic surfactants.

Suitable non-ionic surfactants are alkylamine alkoxylates, amidoamines, alkanolamides, alkylphosphine oxides, N-alkyl glucamides, alkyl glucosides, bile acids, alkyl alkoxylates, sorbitan esters, sorbitan ester ethoxylates, fatty alcohols, fatty acid ethoxylates, ester ethoxylates and polyether siloxanes.

Suitable zwitterionic surfactants are betaines, alkylglycines, sultaines, amphopropionates, amphoacetates, tertiary amine oxides and silicobetaines.

Suitable cationic surfactants are quaternary ammonium salts bearing one or two substituents having 8 to 20 carbon atoms, in particular corresponding tetraalkylammonium salts, alkylpyridinium salts, ester quats, diamidoamine quats, imidazolinium quats, alkoxyalkyl quats, benzyl quats and silicone quats.

In a preferred embodiment of the absorption medium according to the invention, the wetting-promoting additive comprises one or more non-ionic surfactants of general formula $R(OCH_2CHR')_mOH$ having m from 4 to 40, where R is an alkyl radical having 8 to 20 carbon atoms, an alkylaryl radical having 8 to 20 carbon atoms, or a polypropylene oxide radical having 3 to 40 propylene oxide units, and R' is methyl or preferably hydrogen.

In a further preferred embodiment of the absorption medium according to the invention, the wetting-promoting additive comprises a polyether-polysiloxane copolymer which contains more than 10% by weight of $[Si(CH_3)_2O]$ units and more than 10% by weight of $[CH_2CHR''{-}O]$ units, in which R" is hydrogen or methyl. Particular preference is given to polyether-polysiloxane copolymers of the general formulae (IV) to (VI):

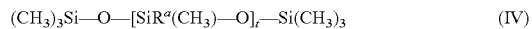  (IV)

  (V)

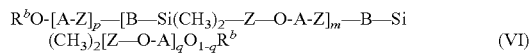  (VI)

where

A is a divalent radical of the formula $-[CH_2CHR^c-O]_r-$,

B is a divalent radical of the formula $-[Si(CH_3)_2-O]_s-$,

Z is a divalent linear or branched alkylene radical having 2 to 20 carbon atoms and is preferably $-(CH_2)_3-$, t=1 to 30, m=2 to 100, p, q=0 or 1, r=2 to 100, s=2 to 100, $R^a$ from 1 to 5 of the radicals $R^a$ are radicals of the general formula $-Z-O-A-R^b-$ and the remaining radicals $R^a$ are methyl, $R^b$ is hydrogen, an alkyl radical or an aliphatic or olefinic acyl radical having 1 to 20 carbon atoms and $R^c$ is hydrogen or methyl.

The wetting-promoting additives are already known to those skilled in the art from the prior art as additives for aqueous solutions and can be produced according to processes known from the prior art.

The absorption medium according to the invention can comprise what are termed activators. By adding activators, the desired separation effect can be further improved. The absorption medium according to the invention preferably comprises primary or secondary amines as activators, which do not have a structure according to formulae (I) to (III). Amines which are suitable for this purpose are preferably amines which have rapid kinetics with respect to binding acid gases, in particular $CO_2$. Preferably, the absorption medium according to the invention comprises activators selected from monoethanolamine, piperazine and 3-(methylamino)-propylamine. The absorption medium according to the invention preferably comprises from 0 to 20% by weight of the activators.

A device according to the invention for separating acid gases, in particular $CO_2$, from a gas mixture comprises an absorption unit, a desorption unit and a circulating absorption medium according to the invention. The apparatuses described above for the absorption in a process according to the invention are suitable as absorption unit of the device according to the invention. The apparatuses described above for the desorption in a process according to the invention are suitable as desorption unit of the device according to the invention. Preferably, the device according to the invention comprises an absorption unit and a desorption unit as known to those skilled in the art from devices for separating acid gases, in particular $CO_2$, from a gas mixture using an alkanolamine.

The examples hereinafter are intended to illustrate the process according to the invention or the absorption medium according to the invention in more detail, without the invention being intended to be restricted to this embodiment.

Example 1

For Producing 4-(3-dimethylaminopropylamino)-2,2,6,6-tetramethylpiperidine 1808.9 g (11.65 mol) of 2,2,6,6-tetramethyl-4-piperidinone and 1191.1 g (11.66 mol) of $N^1,N^1$-dimethyl-1,3-propanediamine are combined in a 4 l reactor and stirred for 2 hours at 60° C. Then, the reaction water is distilled off in vacuum. Thereafter the reaction solution is transferred to an autoclave and admixed with 76 g of Raney nickel. The autoclave is flushed 3 times with 5 bar nitrogen each time. Then, the hydrogenation is carried out by repeated pressurization with 50 bar hydrogen, wherein the reaction mixture is stirred vigorously during the entire reaction time. Then, the reaction mixture is separated by fractional distillation. The product has a boiling point of 130° C. at 4.5 mbar. 2062 g of product could be isolated having a purity of 98.6% and a yield of 72% of theory.

Examples 2-12

On the $CO_2$ Loading and on the $CO_2$ Uptake

In a thermostated apparatus for measuring gas-liquid equilibria, equipped with a pressure control, an absorption medium composed according to the details in Table 1 was charged at a constant temperature and contacted with gaseous carbon dioxide at a constant pressure, wherein pressure and temperature were varied. The content of absorbed $CO_2$ in the loaded absorption medium was determined in each case after the equilibrium state was achieved and the degree of loading was calculated therefrom as a molar ratio of $CO_2$ to amine in the loaded absorption medium. The temperatures and pressures studied and the degrees of loading determined therefor are summarized in Table 2.

TABLE 1

| | Absorption medium | | | | | | |
|---|---|---|---|---|---|---|---|
| | AM 1 | AM 2 | AM 3 | AM 4 | AM 5 | AM 6 | AM 7 |
| | (in % by weight) | | | | | | |
| Water | 70 | 50 | 70 | 70 | 70 | 70 | 70 |
| Monoethanolamine | 30 | 0 | 0 | 0 | 0 | 0 | 0 |
| Methyldiethanolamine | 0 | 50 | 0 | 0 | 0 | 0 | 0 |
| n-Butyl-TAD[1] (amine (B)) | 0 | 0 | 30 | 0 | 15 | 27 | 0 |

TABLE 1-continued

| | Absorption medium | | | | | | |
|---|---|---|---|---|---|---|---|
| | AM 1 | AM 2 | AM 3 | AM 4 | AM 5 | AM 6 | AM 7 |
| | (in % by weight) | | | | | | |
| TAT[2] (amine (A)) | 0 | 0 | 0 | 30 | 15 | 3 | 0 |
| EAE-TAD[3] (amine (A)) | 0 | 0 | 0 | 0 | 0 | 0 | 30 |
| According to the invention | no | no | no | yes | yes | yes | yes |

[1]n-Butyl-TAD: 4-(n-Butylamino)-2,2,6,6-tetramethylpiperidine
[2]TAT: 4-(3-Dimethylamino-propylamino)-2,2,6,6-tetramethylpiperidine or triacetonetriamine
[3]EAE-TAD: 4-(2-Ethylaminoethylamino)-2,2,6,6-tetramethylpiperidine

TABLE 2

| Example | Absorption medium | Temperature (in °C.) | | $CO_2$ partial pressure (in bar) | | Loading (in mol $CO_2$/ mol amine) | | $CO_2$ uptake (in mol $CO_2$/ mol amine) |
|---|---|---|---|---|---|---|---|---|
| | | AS[4] | DS[5] | AS[4] | DS[5] | AS[4] | DS[5] | |
| 2 | AM 1 | 40 | 120 | 1 | 1 | 0.63 | 0.4 | 0.23 |
| 3 | AM 1 | 40 | 120 | 3 | 1 | 0.7 | 0.4 | 0.3 |
| 4 | AM 2 | 40 | 120 | 1 | 1 | 0.65 | 0.09 | 0.56 |
| 5 | AM 2 | 40 | 120 | 3 | 1 | 0.85 | 0.09 | 0.76 |
| 6 | AM 3 | 40 | 110 | 1 | 1 | 1.2 | 0.3 | 0.8 |
| 7 | AM 3 | 40 | 110 | 3 | 1 | 1.7 | 0.3 | 1.4 |
| 8 | AM 4 | 40 | 110 | 1 | 1 | 1.8 | 0.6 | 1.2 |
| 9 | AM 4 | 40 | 110 | 3 | 1 | 2.2 | 0.6 | 1.6 |
| 10 | AM 5 | 40 | 110 | 1 | 1 | 2.2 | 0.5 | 1.7 |
| 11 | AM 5 | 40 | 110 | 3 | 1 | 2.75 | 0.5 | 2.25 |
| 12 | AM 7 | 40 | 110 | 3 | 1 | 2.2 | 0.65 | 1.55 |

[4]AS: Absorber
[5]DS: Desorber $CO_2$ loadings at differing temperatures are shown in Table 2. The temperature of 40° C. corresponds to the loading temperature in the absorber. In this case, depending on gas composition and type of use, different partial pressures of $CO_2$ can be present (e.g. p($CO_2$)=1 bar or p($CO_2$)=3 bar). The temperature of 110° C. or 120° C. corresponds to the desorption temperature at which the solvent is regenerated again in a second apparatus (desorber). Desorption is customarily performed in a pressure range from 1.5 to 2.5 bar, wherein the $CO_2$ partial pressure is approximately 1 bar. At both temperatures (40° C. and 110° C. or 120° C.) the solvent has differing $CO_2$ loadings and the difference between the two values corresponds to the $CO_2$ uptake. The greater this uptake is, the smaller is the solvent stream in the plant. This not only means lower capital costs, since smaller apparatuses are sufficient, but also has a great effect on the desorption temperature to be employed in the desorber.

In comparison with the absorption media of the prior art (AM 1, AM 2 and AM 3), the absorption media according to the invention (AM 4, AM 5 and AM 7) show markedly greater $CO_2$ uptakes. This is equivalent to a saving in regeneration energy, which in turn means a reduction in operating costs, for example with respect to the amount of steam for regenerating the solvent.

Completely surprisingly, the absorption medium AM 5 according to the invention—a mixture of n-butyl-TAD and TAT—in addition shows a markedly higher $CO_2$ uptake than the absorption medium AM 4 according to the invention, which comprises only TAT as amine. Based on the results for absorption media AM 3 and AM 4, a $CO_2$ uptake in the range of values from 0.8 to 1.2 would have been expected for Example 10. The fact that the $CO_2$ uptake in Example 10 improved so markedly could in no way have been predicted and was therefore completely surprising.

In addition, there is the fact that the $CO_2$ uptakes determined in Examples 8 to 12 were carried out at a regeneration temperature of 110° C. Particularly in the case of the absorption media AM 1 and AM 2, regeneration temperatures of 120° C. have been necessary. This means that, by using the absorption media AM 4, AM 5 and AM 7, the regeneration energy is decreased. For operating the plants, two options result therefrom:
 a) A regeneration temperature of 120° C. is retained, and a greater resultant $CO_2$ uptake can be expected owing to the lower $CO_2$ loading at 120° C. This leads to a decrease in the circulation rate of the absorption medium. Circulation rate in the context of this invention is meant to be the frequency by which a defined amount of absorption medium must be circulated in the device according to the invention—an absorption-desorption plant—in order to free a defined amount of a gas mixture having a defined content of $CO_2$ from this $CO_2$.
 b) A regeneration temperature of 110° C. is selected, and this leads to savings in regeneration energy.

Examples 13-15

On Corrosion Behaviour

The corresponding electrochemical analytical method (Tafel plot method) was carried out according to Kladkaew, N et al. in Eng. Chem. Res. 2009, 48, 8913-8919 or according to ASTM G59-97e1. The corresponding results are compiled in Table 4.

TABLE 4

| Example | Absorption medium treated with $CO_2$ gas | Corrosion rate (in mm/year) |
|---|---|---|
| 13 | AM 1 | 1.991 |
| 14 | AM 3 | 0.223 |
| 15 | AM 5 | 0.18 |

The absorption medium AM 5 according to the invention has markedly lower corrosion rates compared with the absorption media of the prior art (AM 1 and AM 3) and thereby increases the service life of the plant and permits the use of more favourable materials, and so the capital costs are decreased.

Examples 16-22

On Phase Separation Behaviour

In a pressure-resistant glass vessel, an absorption medium composed according to the details in Table 5 was charged and saturated with $CO_2$ at 20° C. and atmospheric pressure by adding dry ice or by passing through it a gas mixture of 80% by volume of nitrogen, 6% by volume of oxygen and 14% by volume of $CO_2$. The glass vessel was then closed and the absorption medium loaded with $CO_2$ was slowly heated in an oil bath until separation into two liquid phases occurred, which could be recognized as turbidity of the previously clear mixture. The phase separation temperatures thus determined are summarized in Table 6.

TABLE 5

| | Absorption medium | | | | | | |
|---|---|---|---|---|---|---|---|
| | AM 8 | AM 9 | AM 10 | AM 11 | AM 12 | AM 13 | AM 14 |
| | (in % by weight) | | | | | | |
| Water | 70 | 70 | 70 | 70 | 70 | 65 | 65 |
| n-Butyl-TAD[1] (amine (B)) | 10 | 0 | 0 | 25 | 15 | 30 | 15 |
| n-Propyl-TAD[2] (amine (B)) | 0 | 10 | 0 | 0 | 0 | 0 | 0 |
| Methyl-TAD[3] (amine (B)) | 0 | 0 | 10 | 0 | 0 | 0 | 0 |
| TAT[4] (amine (A)) | 20 | 20 | 20 | 5 | 15 | 5 | 20 |
| According to the invention | yes | yes | yes | yes | yes | yes | yes |

[1] n-Butyl-TAD: 4-(n-butylamino)-2,2,6,6-tetramethylpiperidine
[2] n-Propyl-TAD: 4-(n-propylamino)-2,2,6,6-tetramethylpiperidine
[3] Methyl-TAD: 4-methylamino-2,2,6,6-tetramethylpiperidine
[4] TAT: 4-(3-dimethylamino-propylamino)-2,2,6,6-tetramethylpiperidine or triacetonetriamine

TABLE 6

| | | Phase separation temperature in °C. | |
|---|---|---|---|
| Example | Absorption medium | saturated at 0.14 bar $CO_2$ partial pressure | saturated at 1 bar $CO_2$ partial pressure |
| 16 | AM 8 | n.d. | 107 |
| 17 | AM 9 | n.d. | 115 |
| 18 | AM 10 | n.d. | 119 |
| 19 | AM 11 | 85 | 93 |
| 20 | AM 12 | n.d. | 103 |
| 21 | AM 13 | 95 | 100 |
| 22 | AM 14 | n.d. | 108 | n.d. not determined

For the absorption medium AM 4 that contains only TAT as amine, no phase separation was observed in the saturated state at 1 bar $CO_2$ partial pressure, even on heating to 125° C. The examples show that by choosing the quantitative proportions of TAT and n-alkyl-TAD, the phase separation temperature may be set for the absorption medium loaded with acid gases.

The invention claimed is:

1. A process for absorption of an acid gas from a gas mixture, comprising contacting the gas mixture with an absorption medium, wherein said absorption medium comprises at least water as solvent and at least one amine (A) of formula (I):

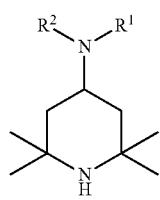
(I)

wherein:
$R^1$=aliphatic radical having 2 to 6 carbon atoms and having at least one amino group;
$R^2$=hydrogen, a $C_{1-4}$ alkyl group or a radical $R^1$.

2. The process of claim 1, wherein said absorption medium comprises at least one amine (A) of formula (II):

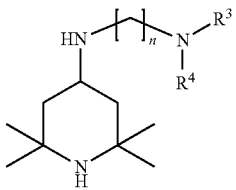
(II)

wherein:
$R^3$=hydrogen or a $C_{1-4}$ alkyl group;
$R^4$=$C_{1-4}$ alkyl group; and
n=2 to 4.

3. The process of claim 2, wherein $R^3$ and $R^4$=methyl and n=3.

4. The process of claim 1, wherein said absorption medium further comprises an amine (B) of formula (III):

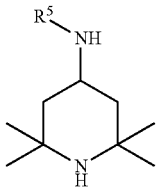
(III)

wherein $R^5$=$C_{1-6}$ alkyl group.

5. The process of claim 2, wherein said absorption medium further comprises an amine (B) of formula (III):

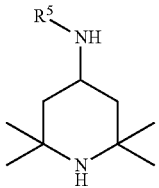
(III)

wherein $R^5$=$C_{1-6}$ alkyl group.

6. The process of claim 1, wherein said absorption medium further comprises a further physical solvent (C).

7. The process of claim 6, wherein said physical solvent (C) is sulpholane.

8. The process of claim 1, wherein said absorption medium comprises:
60 to 80% by weight of water and optionally solvent (C);
1 to 40% by weight of the amine (A); and
0 to 39% by weight of an amine (B) of formula (III):

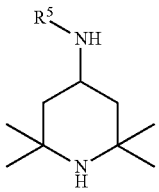
(III)

wherein $R^5$=$C_{1-6}$ alkyl group.

9. The process of claim 8, wherein said absorption medium comprises 60 to 80% by weight of water and solvent (C).

10. The process of claim 1, wherein said absorption medium further comprises corrosion inhibitors, activators, wetting-promoting additives and/or defoamers.

11. The process of claim 1, wherein said gas mixture is natural gas or synthesis gas.

12. The process of claim 1, wherein the partial pressure of the acid gas is from 0.1 bar to 20 bar.

13. The process claim 1, wherein said acid gas is absorbed at a temperature of 20 to 60° C.

14. The process of claim 13, wherein said acid gas is desorbed at a temperature of 60 to 100° C.

15. The process of claim 1, wherein said acid gas comprises carbon dioxide.

16. The process of claim 1, wherein the absorption medium, after it has been contacted with the gas mixture, is heated to a temperature at which a phase separation into an aqueous liquid phase and an organic liquid phase occurs.

17. The process of claim 16, wherein:
a) said acid gas is desorbed from the aqueous liquid phase by reducing the pressure and/or supplying heat;
b) the resulting liquid phase is combined with the organic liquid phase obtained on phase separation; and
c) the combined liquid phases are again, as absorption medium, contacted with the gas mixture.

18. The process of claim 16, wherein, after the phase separation, acid gas is desorbed from the resulting two-phase mixture by stripping with a gas.

19. An amine-containing absorption medium, comprising:
a) at least water as solvent;
b) at least one amine (A) of formula (I):

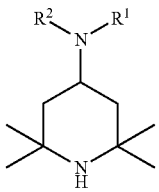

(I)

wherein:
$R^1$=aliphatic radical having 2 to 6 carbon atoms and having at least one amino group; and
$R^2$=hydrogen, a $C_{1-4}$ alkyl group or a radical $R^1$; and
c) an amine (B) of formula (III)

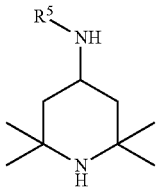

(III)

wherein $R^5$=$C_{1-6}$ alkyl group.

20. A device for separating off acid gas from a gas mixture, said device comprising an absorption unit, a desorption unit and the circulating absorption medium of claim 19.

* * * * *